(12) United States Patent
Lee et al.

(10) Patent No.: US 10,149,883 B1
(45) Date of Patent: Dec. 11, 2018

(54) METHOD OF TREATMENT OF DIABETES-INDUCING KIDNEY FAILURE

(71) Applicant: Chen-Yu Lee, Taipei (TW)

(72) Inventors: Chen-Yu Lee, Taipei (TW); Yan-Chih Liao, Taipei (TW)

(73) Assignee: Chen-Yu Lee, Taipei (TW)

( * ) Notice: Subject to any disclaimer, the term of this patent is extended or adjusted under 35 U.S.C. 154(b) by 42 days.

(21) Appl. No.: 15/642,590

(22) Filed: Jul. 6, 2017

(51) Int. Cl.
| | | |
|---|---|---|
| *A61K 36/00* | (2006.01) | |
| *A61K 36/9068* | (2006.01) | |
| *A61K 36/07* | (2006.01) | |
| *A61K 36/076* | (2006.01) | |
| *A61K 36/284* | (2006.01) | |
| *A61K 36/884* | (2006.01) | |
| *A61K 36/61* | (2006.01) | |
| *A61K 36/714* | (2006.01) | |
| *A61K 36/756* | (2006.01) | |
| *A61K 36/232* | (2006.01) | |
| *A61K 36/481* | (2006.01) | |
| *A61K 36/28* | (2006.01) | |
| *A61K 36/355* | (2006.01) | |
| *A61K 36/88* | (2006.01) | |
| *A61K 36/708* | (2006.01) | |
| *A61K 36/258* | (2006.01) | |

(52) U.S. Cl.
CPC .......... *A61K 36/9068* (2013.01); *A61K 36/07* (2013.01); *A61K 36/076* (2013.01); *A61K 36/232* (2013.01); *A61K 36/258* (2013.01); *A61K 36/28* (2013.01); *A61K 36/284* (2013.01); *A61K 36/355* (2013.01); *A61K 36/481* (2013.01); *A61K 36/61* (2013.01); *A61K 36/708* (2013.01); *A61K 36/714* (2013.01); *A61K 36/756* (2013.01); *A61K 36/88* (2013.01); *A61K 36/884* (2013.01)

(58) Field of Classification Search
CPC ...................................................... A61K 36/00
See application file for complete search history.

(56) References Cited

PUBLICATIONS

Chen-Yu Lee et al., "Integrated TCM and Western Medicine Efficacy in the Treatment of Diabetic Encephalopathy", Dec. 2016, vol. 4, No. 1, pp. 9-33.

*Primary Examiner* — Qiuwen Mi
(74) *Attorney, Agent, or Firm* — Bacon & Thomas, PLLC

(57) ABSTRACT

The present invention is directed to a therapeutic method of treatment of diabetes inducing kidney failure, comprising administering a therapeutically effective amount of Chinese herbal medicine to a subject in need. The Chinese herbal medicine is the decocting extract including the mixture of Grifola, Poria, Atractylodes Lancea Rhizoma, Rhizoma Alismatis, Pimenta officinalis seed, Rhizoma Zingiberis, Radix Aconiti Lateralis Praeparata, Phelloendron amurense bark, Radix Angelicae Sinensis, Radix Astragali, Herb Elephantopus, Honeysuckle Stem, Rhizoma Anemarrhenae, radix Rhubarb, Radix Panax notoginseng, and Radix Ginseng.

9 Claims, No Drawings

METHOD OF TREATMENT OF DIABETES-INDUCING KIDNEY FAILURE

BACKGROUND OF THE INVENTION

1. Field of the Invention

The present invention is directed to a method of treatment of kidney failure; in particular, to a method of treatment of diabetes-inducing kidney failure.

2. Description of Related Art

The application of Chinese herbal medicine in treatment of cancer attracts significant attentions for a long time. In recent years, the Chinese herbal medicine is also gradually applied to treatment of some metabolic diseases, too.

Diabetes mellitus (or diabetes) is a metabolic disease, whose typical symptoms include high blood sugar levels over a prolonged period, and being difficult to maintain the normal value. Other diabetic syndromes and complications include but are not limited to polyphagia, polydipsia, polyuria, blurry vision, headache, fatigue, slow healing of wound, cardiovascular disease, stroke, chronic renal disease, foot ulcer, and retinopathy.

In present time, there is no effective medicine to cure diabetes but the general treatment simply ameliorates the conditions, including administration of hypoglycemic drug, improving diet, lifestyle, and weight loss. Regular diabetes drugs include Biguanides, Thiazolidinediones, Sulfonylureas, and Glycosurics. The effect of these medicines comprises improving sensitivity to insulin, increasing the amount of secretion of insulin, or increasing the excretion of sugar.

Approximate 20-30% of diabetes patients suffer from kidney failure; however, the connection underlying between diabetes mellitus and kidney failure is still vague. The patients of diabetic kidney failure acquire symptoms such as high BUN/CR, nausea, vomiting, loss of appetite, weakness, increasing fatigue, trouble concentrating, and anemia. The typical treatment of diabetic kidney failure comprises intake of drugs of hypertension, hyperglycemia, or dialysis for the severe patients.

SUMMARY OF THE INVENTION

One of the objects of the present application is to provide a method of the treatment of kidney failure.

Another objective of the present application is to provide a method of treatment of diabetes-inducing kidney failure.

The method of treatment of diabetes-inducing kidney failure comprises administering a therapeutically effective amount of Chinese herbal medicine to a subject in need; wherein the Chinese herbal medicine is an extract of a first mixture comprising:

Grifola, Poria, Atractylodes Lancea Rhizoma, Rhizoma Alismatis, Pimenta officinalis seed, Rhizoma Zingiberis, Radix Aconiti Lateralis Praeparata, Phelloendron amurense bark, Radix Angelicae Sinensis, Radix Astragali, Herb Elephantopus, Honeysuckle Stem, Rhizoma Anemarrhenae, radix Rhubarb.

In a preferred embodiment of the present invention, the Chinese herbal medicine is prepared by following steps:

providing the first mixture; mixing the first mixture and water to form a second mixture; heating the second mixture to obtain a crude extract; and filtering the crude extract and retaining the liquid, to obtain the Chinese herbal medicine.

In a preferred embodiment of the present invention, the Chinese herbal medicine is the extract of the first mixture comprising: 4-6 parts by weight of Grifola, 12-14 parts by weight of Poria, 4-6 parts by weight of Atractylodes Lancea Rhizoma, 16-20 parts by weight of Rhizoma Alismatis, 4-6 parts by weight of Pimenta officinalis seed, 2-4 parts by weight of Rhizoma Zingiberis, 2-4 parts by weight of Radix Aconiti Lateralis Praeparata, 10-12 parts by weight of Phelloendron amurense bark, 1-3 parts by weight of Radix Angelicae Sinensis, 17-19 parts by weight of Radix Astragali, 5-7 parts by weight of Herb Elephantopus, 5-7 parts by weight of Honeysuckle Stem, 4-6 parts by weight of Rhizoma Anemarrhenae, 1-3 parts by weight of radix Rhubarb.

In a preferred embodiment of the present invention, the part by weight of the first mixture is 3.75 gram per part.

In a preferred embodiment of the present invention, the first mixture further comprises radix Panax notoginseng, radix Ginseng, or the combination of thereof.

In a preferred embodiment of the present invention, the treatment of diabetes-inducing kidney failure is the treatment of high blood creatine, azotemia, hyperglycemia, constipation, oliguria, and swollen.

In a preferred embodiment of the present invention, the method is the treatment of uremia of kidney failure.

In a preferred embodiment of the present invention, the Chinese herbal medicine is administered via oral administration, enteral administration, or intravenous injection.

In a preferred embodiment of the present invention, the Chinese herbal medicine further comprises pharmaceutically acceptable carrier, stabilizer, diluent, dispersant, suspending agents, thickening agent, or excipient, or the combination thereof.

DETAILED DESCRIPTION OF THE PREFERRED EMBODIMENT

The features of the present invention are set forth with particularity in the appended claims. A better understanding of the features and advantage thereof will be demonstrated by reference to the following detailed description that sets forth illustrative embodiments, in which the principles of the invention are employed.

Certain Pharmaceutical and Medical Terminology

Unless otherwise specified, the following terms used in the specification and claims have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology can be employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described. Unless otherwise indicated, all materials employed in the present invention are available in the ordinary markets.

The term "diabetes" or "diabetes mellitus", as used herein, refers to type 1 diabetes, type 2 diabetes, gestational diabetes, or diseases and conditions having typical signs or symptoms of diabetes mellitus.

The term "carrier" or "excipient", as used herein, refers to relatively nontoxic chemical compounds or agents that facilitate the incorporation of a compound into cells or tissues without interfering the effect of the treatment.

The term "diluent", as used herein, refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The aforementioned vehicles can further comprise aromatics, buffering agents, binders, colorants, disintegrants, emulsifiers, extenders, flavor-improving agents, gellants, glidants, preservatives, skin-penetration enhancers, solubilizers, stabilizers, dispersing agents, suspending agents, sweeteners, tonicity agents, viscosity-increasing agents, or the combination thereof.

The term "pharmaceutically acceptable", as used herein, refers to the compounds, formulations, composition, and/or dose form, within the scope of reasonable medical judgment, suitable for contacting with the suffered subject, without undue detrimental effect, toxicity, irritation, allergic response, or any conditions or complications on the general health of the subject being treated, and commensurate with a reasonable benefit/risk ratio.

The term "effective amount" or "therapeutically effective amount", as used herein, refers to a sufficient amount of an agent or a compound being administered which will relieve one or more of the symptoms of the disease or condition being treated to some extent; the result thereof can be reduction and/or alleviation of the signs, symptoms, or causes of a disease, or any other desired alteration of a biological system. For example, an "effective amount" for therapeutic uses is the amount of the composition as disclosed herein required to provide a clinically significant decrease in disease symptoms. An appropriate "effective" amount in any individual case may be determined using techniques, such as a dose escalation study.

The term "enhance", "enhancing", or the like, as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

The terms "treat," "treating", "treatment", or the like, as used herein, include alleviating, abating or ameliorating at least one symptom of a disease or condition, preventing disease progression, inhibiting the disease or condition, e.g., arresting the development of the disease or condition, relieving the disease or condition, causing regression of the disease or condition, relieving the condition caused by the disease or condition, or reducing the sign or symptoms of the disease or condition either prophylactically and/or therapeutically.

The term "resistance" or the like, as used herein, refers to the regression of the sensitivity to certain medicine, increment of therapeutically effective amount compared to the expected effect, after a series of course of treatment are taken by a subject in need. The term "drug-resistance" or the like, as used herein, is resistance to a single drug or multidrug resistance.

The term "tolerance", as used herein, refers to the adaptive reaction or reduced reaction of cell, tissue, organisms to the drug, after a series of course of treatment are taken by a subject in need, and leading to symptoms of withdrawal upon abruption or decrease in intake of medicine.

General Consideration for Combination Treatments

The term "combination therapy" or the like, as used herein, refers to giving or administering to a suffered subject at least two selected pharmaceuticals, further comprising a course of treatment, via the same or different routes simultaneously, concurrently or sequentially.

In general, the compositions described herein and, in embodiments where combinational therapy is employed based on the mode of action described herein, other agents do not have to be administered in the same pharmaceutical composition; and in some embodiments, because of different physical and chemical characteristics, they are administered by different routes. In some embodiments, the initial administration is made according to established protocols, and then, based upon the observed effects, the dosage, modes of administration and times of administration is modified by the skilled clinician.

In the embodiment herein, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

The term "combination" or the like, as used herein, means a product that results from combining more than one active pharmaceutical and includes both fixed and non-fixed combinations of the active ingredients. The term "fixed combination" means that the active pharmaceuticals are administered to a patient simultaneously in the form of a single entity or dosage. The term "non-fixed combination" means that the active pharmaceuticals are administered to a patient as separate entities either simultaneously, concurrently or sequentially with no specific intervening time limits, wherein such administration provides effective levels of the pharmaceuticals in the body of the patient. The latter may also be applied to cocktail therapy, e.g. the administration of three or more active ingredients.

The dose forms of the Chinese herbal medicine provided in the present invention include but are not limit to solution, emulsion, suspension, powder, tablet, pill, lozenge, troche, chewing gum, capsule, or any dose form which is suitable for the Chinese herbal medicine provided herein.

The present invention provides a method of treatment of insulin-resistance diabetes mellitus, comprising administering a therapeutically effective amount of Chinese herbal medicine to a subject in need, wherein the Chinese herbal medicine is an extract of a first mixture comprising Grifola, Poria, Atractylodes Lancea Rhizoma, Rhizoma Alismatis, Pimenta officinalis seed, Rhizoma Zingiberis, Radix Aconiti Lateralis Praeparata, Phelloendron amurense bark, Radix Angelicae Sinensis, Radix Astragali, Herb Elephantopus, Honeysuckle Stem, Rhizoma Anemarrhenae, radix Rhubarb, Radix Panax notoginseng, and Radix Ginseng.

In an embodiment, the Chinese herbal medicine can be co-administered with another pharmaceutical composition according to the method of treatment of drug-resistance diabetes mellitus. In a specific embodiment, the Chinese herbal medicine and another pharmaceutical composition are administered simultaneously, concurrently or sequentially.

In an embodiment of the present invention, the pharmaceutical composition said above comprises the pharmaceuticals for treating diabetes disclosed in the prior art, which include, but are not limited to, insulin and the modifiers thereof; biguanide such as metformin, pheformin, and buformin; thiazolidinediones such as rosiglitazone, pioglitazone, and troglitazone; sulfonylurea such as glimepiride, glyburide, glipizide, glipizide, chloropropamide, and tolbutamide; meglitinides such as repaglinide, nateglinide; α-glucosidase inhibitors such as miglitol, acarbose, and voglibose; HMG CoA reductase inhibitor such as mevastatin, lovastatin, simvastatin, atorvastatin, and pitavastatin; SGLT2 inhibitor such as Dapagliflozin, Empagliflozin, Canagliflozin, Ipragliflozin, and Tofogliflozin; DPP-4 inhibitors such as sitagliptin, vildagliptin, saxagliptin, linagliptin, dutogliptin, gemigliptin, alogliptin, and teneligliptin.

The method according to the present invention is the treatment of diabetes mellitus and the complications, syndromes, metabolic disorder, or conditions, including but not limited to type 1 diabetes, type 2 diabetes, gestational diabetes, beta cell genetic deficiency, diabetic ketoacidosis, atherosclerosis, cardiovascular diseases, high blood sugar, hypertension, hyperlipidemia, obesity, acute or chronic renal failure, retinopathy, diabetic foot ulcer, insulin resistance, albuminuria, hyperuricemia, swollen, decreased glucose tolerance. In particular, the method is the treatment of drug-resistance diabetes mellitus.

The foregoing scopes are merely suggestive, as the number of variables in regard to an individual treatment regime is large, and considerable excursions from these recommended values are not uncommon. Such dosages, indication, administration, and intake may be altered depending on a number of variables, not limited to the activity of the compound used, the disease or condition to be treated, the mode of administration, the requirements of the individual subject, the severity of the disease or condition being treated, and the judgment of the practitioner.

Preparation of the Herbal Material and the Chinese Herbal Medicine.

The present invention is directed to an use of Chinese herbal medicine which includes the extract of a first mixture that mixes the following components: 4-6 parts by weight of Grifola (*Polyporus umbellatus*), 12-14 parts by weight of Poria (*Wolfiporia cocos*), 4-6 parts by weight of Atractylodes Lancea Rhizoma, 16-20 parts by weight of Rhizoma Alismatis (*Alisma orientalis*), 4-6 parts by weight of Pimenta officinalis seed, 2-4 parts by weight of Rhizoma Zingiberis (*Zingibor officinale*), 2-4 parts by weight of Radix Aconiti Lateralis Praeparata (*Acontium carmichaeli*), 10-12 parts by weight of Phelloendron amurense bark, 1-3 parts by weight of Radix Angelicae Sinensis, 17-19 parts by weight of Radix Astragali (*Astragalus membranaceus*), 5-7 parts by weight of Herb Elephantopus (*Elephantopus scaber*), 5-7 parts by weight of Honeysuckle Stem (*Lonicerae Japonicae*), 4-6 parts by weight of Rhizoma Anemarrhenae (*Anemarrhena asphodeloides*), 1-3 parts by weight of radix Rhubarb (*Rheum palmatum, R. tanguticum,* or *R. officinale*), 2-4 parts by weight of Radix Panax notoginseng, and 2-4 parts by weight of Radix Ginseng (*Panax ginseng*); wherein it is a daily dose of the Chinese herbal medicine when the part by weight of the first mixture is 3.75 g per part.

The preparation method of the Chinese herbal medicine is provided as follows.

The components of the first mixture are heated and extracted in a solvent; wherein the component of the first mixture can be optionally grinded before extraction to achieve the best extraction outcome, except that raw long gu powder, Haematitum powder, and Magnetitum powder should be extracted in powder. The preferred solvent of the extraction is water, ethanol, DMSO (Dimethyl sulfoxide), or the combination thereof.

In a preferred embodiment of the present invention, the components of the daily dose of the Chinese herbal medicine are dissolved in 1,600 ml water to obtain a second mixture; the second mixture is decocted at 100-120° C. for 1 hour and then the residue of decoction is filtered out to obtain the liquid extract. Preferably, the liquid extract is equally divided into 3 doses for ter in die administration. Preferably, the second mixture is decocted at 100-120° C. for 1 hour and then the volume of the liquid extract after filtration is 450 ml.

Furthermore, the preparation method of the Chinese herbal medicine can include the step of concentration as follows: after the residue of the extract is filter out, the liquid extract is condensed by vacuum or low pressure concentration under the condition of 50-60° C. and 20-40 torr, in order to obtain the condensate; preferably, the volume of the condensate is $\frac{1}{10}$-$\frac{1}{20}$ volume of the liquid extract.

Furthermore, the corn starch used as an excipient is added to the condensate to obtain herbal paste; wherein the quantity of the corn starch depends on the stability of condensate; wherein the paste is optionally subject to granulation by spray-drying method.

Example 1: Patient 1

The diabetes patient of example 1 was diagnosed to have the condition including BUN/CR=52/9.7, high GLU(AC), and administering insulin approximately 20-30 U for one day. Additional symptoms include confusion (disable to concentrate), swollen, oliguria; kidney failure-inducing deregulations of blood oxygen and blood nitrogen also interfere central nerve system and contribute to constipation.

The treatment for the patient in example 1 comprised: daily administration of the daily dose of the Chinese herbal medicine according to the present invention for a period of 3 consecutive days; specifically, a daily dose of Chinese herbal medicine was equally divided for ter in die administration.

After the 3 days course of treatment (administering daily dose for each day), the outcome of the condition of the diabetes patient included:

CR reduced to 8.4, and GLU(AC) reduced to 50 approximately. No insulin was needed during the course of treatment. The patient was able to normally urinate approximately 2,400 ml per day, and was able to concentrate; further, constipation and swollen were alleviated.

Example 2: Patient 2

The diabetes patient of example 2 was diagnosed to have the condition including BUN/CR=26.8/1.1, GLU(AC) 186, and administering insulin approximately 10-20 U for one day. Additional symptoms include confusion (disable to concentrate), swollen, oliguria.

The treatment for the patient in example 1 comprised: daily administration of the daily dose of the Chinese herbal medicine according to the present invention for a period of 5 consecutive days; specifically, a daily dose of Chinese herbal medicine was equally divided for ter in die administration. Particularly, the daily dose of the Chinese herbal medicine in example 2 was the extract of the first mixture; wherein the first mixture additionally included 5 parts by weight of rhizoma Coptidis (*Coptis chinensis, C. deltoidea,* or *C. teeta*).

After the 5 days course of treatment (administering daily dose for each day), the outcome of the condition of the diabetes patient included:

BUN/CR reduced to 15.4/0.9, and GLU(AC) reduced to 150 approximately. No insulin was needed during the course of treatment. The patient was able to normally urinate approximately 2,000 ml per day, and was able to concentrate; further, swollen were alleviated.

While the preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents are covered thereby.

What is claimed is:

1. A method of treatment of diabetes-inducing kidney failure, comprising administering a therapeutically effective amount of Chinese herbal medicine to a subject in need;
    wherein the Chinese herbal medicine is an extract of a first mixture comprising
    Grifola, Poria, Atractylodes Lancea Rhizoma, Rhizoma Alismatis, Pimenta officinalis seed, Rhizoma Zingiberis, Radix Aconiti Lateralis Praeparata, Phellodendron amurense bark, Radix Angelicae Sinensis, Radix Astragali, Herb Elephantopus, Honeysuckle Stem, Rhizoma Anemarrhenae, and radix Rhubarb.

2. The method as claimed in claim 1, wherein the Chinese herbal medicine is prepared by following steps:
    providing the first mixture;
    mixing the first mixture and water to form a second mixture;
    heating the second mixture to obtain a crude extract; and
    filtering the crude extract and retaining the liquid, to obtain the Chinese herbal medicine.

3. The method as claimed in claim 1, wherein the Chinese herbal medicine is the extract of the first mixture comprising: 4-6 parts by weight of Grifola, 12-14 parts by weight of Poria, 4-6 parts by weight of Atractylodes Lancea Rhizoma, 16-20 parts by weight of Rhizoma Alismatis, 4-6 parts by weight of Pimenta officinalis seed, 2-4 parts by weight of Rhizoma Zingiberis, 2-4 parts by weight of Radix Aconiti Lateralis Praeparata, 10-12 parts by weight of Phellodendron amurense bark, 1-3 parts by weight of Radix Angelicae Sinensis, 17-19 parts by weight of Radix Astragali, 5-7 parts by weight of Herb Elephantopus, 5-7 parts by weight of Honeysuckle Stem, 4-6 parts by weight of Rhizoma Anemarrhenae, and 1-3 parts by weight of radix Rhubarb.

4. The method as claimed in claim 3, wherein the part by weight of the first mixture is 3.75 gram per part.

5. The method as claimed in claim 1, wherein the first mixture further comprises radix Panax notoginseng, radix Ginseng, or the combination of thereof.

6. The method as claimed in claim 1, wherein the treatment of diabetes-inducing kidney failure is the treatment of high blood creatine, azotemia, hyperglycemia, constipation, oliguria, and swollen.

7. The method as claimed in claim 1, wherein the method is the treatment of uremia of kidney failure.

8. The method as claimed in claim 1, wherein the Chinese herbal medicine is administered via oral administration, enteral administration, or intravenous injection.

9. The method as claimed in claim 1, wherein the Chinese herbal medicine further comprises pharmaceutically acceptable carrier, stabilizer, diluent, dispersant, suspending agents, thickening agent, excipient, or the combination thereof.

* * * * *